(12) United States Patent
Nassar (10) Patent No.: US 11,578,351 B2
(45) Date of Patent: *Feb. 14, 2023

(54) METHODS AND MATERIALS FOR DETECTION OF BIOLOGICALS

(71) Applicant: RAN Biotechnologies, Inc., Beverly, MA (US)

(72) Inventor: Roger A. Nassar, Marblehead, MA (US)

(73) Assignee: RAN Biotechnologies, Inc., Beverly, MA (US)

( * ) Notice: Subject to any disclaimer, the term of this patent is extended or adjusted under 35 U.S.C. 154(b) by 92 days.

This patent is subject to a terminal disclaimer.

(21) Appl. No.: 16/846,509

(22) Filed: Apr. 13, 2020

(65) Prior Publication Data
US 2020/0239929 A1    Jul. 30, 2020

Related U.S. Application Data

(63) Continuation of application No. 14/773,059, filed as application No. PCT/US2014/026587 on Mar. 13, 2014, now Pat. No. 10,640,804.

(60) Provisional application No. 61/784,820, filed on Mar. 14, 2013.

(51) Int. Cl.
| | | |
|---|---|---|
| *C12Q 1/04* | (2006.01) | |
| *G01N 21/78* | (2006.01) | |
| *G01N 33/543* | (2006.01) | |
| *B82Y 15/00* | (2011.01) | |

(52) U.S. Cl.
CPC ............... *C12Q 1/04* (2013.01); *G01N 21/78* (2013.01); *G01N 33/54313* (2013.01); *B82Y 15/00* (2013.01); *Y02A 50/30* (2018.01)

(58) Field of Classification Search
CPC .... C12Q 1/04; G01N 21/78; G01N 33/54313; B82Y 15/00; Y02A 50/30
See application file for complete search history.

(56) References Cited

U.S. PATENT DOCUMENTS

| | | |
|---|---|---|
| 5,612,043 A | 3/1997 | Deprez et al. |
| 6,638,749 B1 | 10/2003 | Beckman et al. |
| 10,105,681 B2 | 10/2018 | Nassar |
| 2006/0002852 A1 | 1/2006 | Saltzman et al. |
| 2006/0292555 A1 | 12/2006 | Xu et al. |
| 2007/0141727 A1 | 6/2007 | Huang et al. |
| 2008/0070274 A1 | 3/2008 | Lee et al. |
| 2010/0015633 A1 | 1/2010 | Lu et al. |
| 2010/0075314 A1 | 3/2010 | Garimella et al. |
| 2010/0105112 A1 | 4/2010 | Holtze et al. |
| 2011/0027854 A1 | 2/2011 | Suda et al. |
| 2011/0117596 A1 | 5/2011 | Mattiasson et al. |
| 2012/0018382 A1 | 1/2012 | Stein |
| 2012/0040905 A1 | 2/2012 | Perret et al. |

FOREIGN PATENT DOCUMENTS

| | | |
|---|---|---|
| CN | 1243444 A | 2/2002 |
| EP | 73611 | 3/1983 |
| EP | 230768 | 8/1987 |
| WO | WO 98-31383 | 7/1998 |
| WO | WO 2007-095279 | 8/2007 |
| WO | WO 2014-151836 | 9/2014 |

OTHER PUBLICATIONS

Deniger et al.; Targeting and penetration of virus receptor bearing cells by nanoparticles coated with envelope proteins of Moloney murine leukemia virus.;Nano Lett. Nov. 2006; 6(11):2414-21.
Gubula et al.; Kinetics of immunoassays with particles as labels: effect of antibody coupling using dendrimers as linkers; Analyst; 2011; 2533-2541.
Kalahnikova et al.; Development of a strategy of influenza virus separation based on pseudoaffinity chromatography on short monolithic columns. Analytical Chem. 80 (6); 2008; 2188-98.
Li et al.; Carbohydrate-functionalized chitosan fiber for influenza virus capture. Biomacromolecules; 12 (11); 2011; 3962-69.
Medintz et al.; Proteolytic activity monitored by fluorescence resonance energy transfer through quantum-dot-peptide conjugates; Nat. Mat.; V. 5; 581-9. 2006.
Nassar et al.; Removing human immunodeficiency virus (HIV) from human blood using immobilized heparin. Biotech. Let.; 34 (5); 2012; 853-6.
Oberg et al.; Templating gold surfaces with function: a self-assembled dendritic monolayer methodology based on monodisperse polyester scaffolds. Langmuir; Jan. 8, 2013; 29 (1); 456-65 (Epub Dec. 19, 2012).
Otsuka et al.; Quantitive and reversible lectin-induced association of gold nanoparticles modified with a-lactosyl-w-mercapto-poly)ethylene glycol); J. Am. Chem. Soc.; 123 (4); 2001; 8226-30.
Pissuwan et al.; Prospects for gold nanorod particles in diagnostic and therapeutic applications. Biotechnol. Genet. Eng. Rev. V 25; 2008; 93-112.
Prencipe et al.; PEG branched polymer for functionalization of nanomaterials with ultralong blood circulation. J Am Chem Soc.; Apr. 8, 2009; 131 (13); 4783-7. (Epub Feb. 3, 2009 at http://arxiv.org/pdf/0901.4961. Total pp. 1-18).
Rusnati et al.; Interaction of HIV-1 Tat protein with heparin. Role of the backbone structure, sulfation, and size.J Biol Chem; Apr. 25, 1997; v272; 11313-20.
Simons et al.; Monodispere perfluorohexane emulsions for targeted ultrasound contrast imaging. J. Mat. Chem; V. 20; 3918-23. Mar. 12, 2010.
Torchilin et al.; p-Nitrophenylcarbonyl-PEG-PE-liposomes: fast and simple attachment of specific ligands, including monoclonal antibodies, to distel ends of PEG chains via p-nitrophenylcarbonyl groups. Biochimica et Biophysica Acta; Feb. 2001; 397-411.

*Primary Examiner* — Satyendra K Singh
(74) *Attorney, Agent, or Firm* — Wolf, Greenfield & Sacks, P.C.

(57) ABSTRACT

Methods of detecting biologicals in samples is provided herein. The detection is based on the formation of aggregates. The disclosed compositions include labeling particles and/or aggregating particles. The labeling particles and the aggregating particles may each include a receptor bound to the particle. The receptor can be either directly attached to the particle or indirectly attached to the particle through a linker. One method of detection may be visual and another may include advanced quantification of the formed aggregates.

20 Claims, 10 Drawing Sheets

Chitosan attachment to PGMA:

Figure 3A

Heparin attachment to Sepharose®:

Figure 3B

Heparin attachment to Sand:

Heparin attachment to sand through a branched linker:

Figure 4A

Heparin attachment to Sepharose® through a branched linker:

Figure 4B

Heparin attachment to PGMA through branched linkers:

Figure 4C

Heparin attachment to gold nanoparticles through a branched linker:

Figure 4D

When X=O and Y=O, the product is a carbonate derivative.
When X=NH and Y=O, the product is a carbamate derivative.
When X=NH and Y=NH, the product is a urea derivative.

Figure 5

Change in the color of materials upon capturing target biological, such as microbes

METHODS AND MATERIALS FOR DETECTION OF BIOLOGICALS

RELATED APPLICATIONS

The present application is a continuation of U.S. patent application Ser. No. 14/773,059, filed Sep. 4, 2015, which is a U.S. National Stage Application of PCT Application No. PCT/US2014/026587, filed Mar. 13, 2014, which claims benefit to U.S. Provisional Application No. 61/784,820, filed Mar. 14, 2013, which is also herein incorporated by reference in its entirety.

FIELD

The present disclosure is directed to materials designed to detect biologicals in fluids and on surfaces and to quantification of their concentrations by forming detectable and quantifiable aggregates, and to methods of manufacturing and using the same.

BACKGROUND

Considerable resources are expended each year to measure and detect microorganisms and biologicals. Ensuring products, public areas, blood and tissue banks, air and water supplies are free of microbial contamination is a major public concern. The occurrence of microorganism and harmful biological contamination in any of these is a major health risk and detection and control thereof are a necessity.

Furthermore, there exists no assay for direct detection of bacteria in samples, such as body fluids, and for diagnosis of infections. Current methods instead diagnose indirectly, for example, by urinalysis, to determine specifically the presence of nitrites, leukocytes, or leukocyte esterase and chemical testing for glucose or pH. Diagnosis of an infection, if confirmed, is done so by bacterial culture, which can be laborious and time consuming. Similarly, there is no direct test for bacteria in cerebrospinal fluid, which could be used for the rapid diagnosis of bacterial meningitis, a rapidly progressing infection of the central nervous system, which is typically fatal if antibiotic treatment is not initiated promptly. Culture methods are too slow to be of use in diagnosing such infections.

Conventional detection methods may also be misleading and do not provide rapid results allowing for immediate action. While current methods may be effective tools to detect and quantify some types of microorganisms, most methods are culture-based or, if developed, molecular-based techniques for specific microorganisms and biologicals. However, these methods can be difficult and time-consuming. In addition, many microorganisms fail to have specific, reliable detection methods, such as many viruses. Some microorganisms also may pose too hazardous for handling, so no detection method is available.

Many tests exist for sensitive detection of a broad spectrum of various bacterial species based on the detection of specific bacterial antigens. However, the tests are limited since they cannot be applied directly for testing of samples where the spectrum of bacterial pathogens is unknown. Also, the tests include an additional step for pre-enrichment of biological. Such a step can take one-to-three days, before performing the advertised tests. Thus, there remains a need for the development of a detection method capable of detecting a broad spectrum of microorganisms, known and unknown, that is easy to employ, fast and accurate.

SUMMARY

The present disclosure provides methods of manufacturing and using labeling particles and formulations to detect biologicals in target samples. One method of detection may be visual as a result of the attachment of biologicals to labeling particles. The resulting biological-particle complexes may be physically separated from the sample using such methods as magnetic separation, filtration or decantation. The visual detection methods may be performed with a naked eye. Other detection methods can be used to qualify or quantify biologicals.

Some embodiments pertain to methods of detecting a biological including the steps of passing or mixing a sample comprising the biological over or with a labeling particle comprising a particle and receptor bound to the particle and detecting the biological by adsorbing the biological to the labeling particle. The particle can be of various sizes of, for example, metallic nano-particles. The receptor can be any chemical moiety known or expected to bind to target biologicals. In one exemplary embodiment, the composition can include a linker bridging between the particle and the receptor. The linker is covalently bonded to the particle and the receptor, and it can be a linear or branched molecule or polymer. In addition, the target biological can be for example a microbe, protein, or a blood product. A pre-enrichment of the target biological is not required.

Some embodiments pertain to methods of detecting a biological including the steps of passing or mixing a sample comprising the biological over or with a labeling particle and an aggregating particle, both comprising a particle and receptor bound to the particle and detecting the biological by adsorbing the biological to the labeling particle and to the aggregating particle. One advantage of using the aggregating particle is to increase the size of the resulting biological-particle aggregate. The labeling particle and the aggregating particle can contain various sizes of agarose, sand, textile, metallic particles, magnetic particles, or combinations thereof. The receptor in the labeling particle and/or the aggregating particle can be any chemical moiety known or expected to bind to target biologicals. In one exemplary embodiment, the composition of the labeling particle and/or the aggregating particle can include a linker bridging between the particle and the receptor. The linker is covalently or physically bonded to the particle and the receptor, and it can be a linear or branched small molecule or polymer. The labeling particle and the aggregating particle can contain the same or different linker and/or receptor. In addition, the target biological can be for example a microbe, protein, or a blood product.

The methods of detecting a biological can also include visual detection of the biological adsorbed to the labeling particle and/or aggregating particle as one method of detection. This visual detection can take place in the fluids or on the surfaces to be tested.

In some embodiments, the method of detecting a biological can include filtering the biological adsorbed to the labeling and/or aggregating particle through a filtering setup as another method of detection. In some embodiments, the method can include separating the biological adsorbed to the magnetic particle with a magnetic separator as another method of detection.

The methods can also include qualifying or quantifying the biological, or combinations thereof, adsorbed to the labeling particle or aggregating particle, or combinations thereof, as one method of detection. The detection of the biological-particle aggregate is achieved with a naked eye or electronically, using tools, softwares and applications capable of qualifying and quantifying colors and their intensities. Such tools can include optical density measurement devices and softwares and color intensity measurement devices and softwares.

The present disclosure also provides methods of manufacturing a labeling particle and/or an aggregating particle including immobilizing a receptor on a particle. The receptor can be heparin or lactose.

BRIEF DESCRIPTION OF THE DRAWINGS

The appended drawings have been included herein so that the above-recited features, advantages and objects of the disclosure will become clear and can be understood in detail. These drawings form a part of the specification. It is to be noted, however, that the appended drawings illustrate suitable embodiments and should not be considered to limit the scope of the disclosure.

DESCRIPTION

Point-of-use detection is performed at the place where a product or a service is actually used. Major benefits are obtained when detection of biologicals is achieved at the point-of-use. Examples of such benefits include limiting or avoiding exposure to infected fluids in remote or poor areas where access to appropriate tests and detection methods is not feasible, detecting infected supplies of blood and their products prior to transfusion, and alerting to the presence of infectious particles in the air or on surfaces. Another example is diagnosing abnormal compositions of bodily fluids at the point-of-test and alerting the patient to take actions against diseases immediately after their onset. Such early detection methods can speed recovery and reduce costs associated with medical treatments.

Detection of biologicals using minimal materials and devices is extremely attractive for point-of-use diagnostics. While nanoparticle-based technologies may be useful, the two main approaches are based on antigen-antibody interactions and recognition of nucleic acids. Both techniques require expensive devices and reagents.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

The disclosed methods and materials allow visual detection of target biologicals. In the presence of labeling particles, e.g. functionalized nanoparticles, target biologicals can trigger the formation of aggregates that absorb, reflect or scatter light, or any combination thereof. Also, the optional presence of aggregating particles in the formulation composed of labeling particles and biological can accentuate the signal that is due to absorption, reflection, or scattering of light, or combinations thereof. Such smart materials may provide critical information on biologicals in fluids at the point-of-use. Ultimately, the intensity of the color of the aggregates can be correlated with the concentration of specific biologicals. The method can be similar to "a litmus test for biologicals."

The term "biologicals" as used herein refers to living organisms and their products, including, but not limited to, cells, tissues, tissue products, blood, blood products, proteins, vaccines, antigens, antitoxins, viruses, microorganisms, fungi, yeasts, algae, bacteria, etc. One example of a biological can include microorganisms, such as pathogenic or a non-pathogenic bacteria. Another example of biologicals can include viruses, viral products, virus-imitating entities, or any combination thereof.

A "microorganism" (i.e., a microbe) as used herein can be a single cell or multicellular organism and includes organisms such as prokaryotes (e.g., bacteria and archaea), eukaryotes (e.g., protozoa, fungi, algae, microscopic plants and animals), and viruses. For example, the bacteria can be gram negative or gram positive. In some embodiments, the microorganism is selected from *Staphylococcus aureus, Streptococcus, Escherichia coli (E. coli), Pseudomonas aeruginosa, mycobacterium*, adenovirus, rhinovirus, smallpox virus, influenza virus, herpes virus, human immunodeficiency virus (HIV), rabies, chikungunya, severe acute respiratory syndrome (SARS), malaria, dengue fever, tuberculosis, meningitis, typhoid fever, yellow fever, ebola, shingella, listeria, yersinia, West Nile virus, protozoa, fungi, *Salmonella enterica, Candida albicans, Trichophyton mentagrophytes*, poliovirus, *Enterobacter aerogenes, Salmonella typhi, Klebsiella pneumonia, Aspergillus brasiliensis*, and methicillin resistant *Staphylococcus aureus* (MRSA), or any combination thereof.

The disclosed methods and materials can detect biologicals by forming visible aggregates, such as those that are visible to the naked eye. Light scattering, absoption, reflection, or any combination thereof, of labeling particles can be used to detect target biologicals. The aggregating particles and other particles can also be used in light scattering, absorbing, or reflecting formulations, or any combination thereof, to detect target biologicals.

The present disclosure provides methods to produce labeling nanoparticles that exhibit physical differences between the presence and absence and upon changes in the concentration of target biologicals. Such differences can be visually detected, such as with the naked eye, or can be qualified and quantified using tools, softwares and applications capable of qualifying and quantifying colors and their intensities. One example of labeling particles can include magnetic or metallic nanoparticles, such as gold nanoparticles. The absence of the target biologicals may also inhibit the formation of such aggregates.

In one embodiment, "labeling particles" can bind to target biologicals and form aggregates. In some embodiments, the resulting aggregates can scatter, absorb and/or reflect light for visual detection. In some embodiments, the aggregates can be separated by such physical separation techniques as magnetic, filtration, decantation, or phase separation process, or any combination thereof. Other separation techniques may also be used that are known by one who is skilled in the art.

Some embodiments include "aggregating particles" to accentuate the signal that results from the labeling particles bound to biologicals. The aggregating particles can be used to increase the size of the aggregate. Such increases can lead to easier detection and more accurate differentiation between different concentrations of biologicals (FIG. 1). Examples of such aggregating particles can include material complexes, like functionalized sand, functionalized agarose, and functionalized polymers that are insoluble in the examined fluid.

Examples of the three main components of the labeling and aggregating particles include: 1) particles, that can be of various sizes of agarose, sand, textiles (such as cellulose/cotton, wool, nylon, polyester), metallic particles (including nanoparticles, such as gold nanoparticles or silver nanoparticles), magnetic particles (including nanoparticles), glass, fibergalss, silica, wood, fiber, plastic, rubber, ceramic, percelain, stone, marble, cement, biological polymers, natural polymers and synthetic polymers [such as Poly(glycidyl methacrylate) (PGMA)], or any combination thereof; 2) receptors, such as lactose (natural and synthetic) and its derivatives (such as sialyllactose), mono- and poly-saccharides, heparin and chitosan, or any combination of multiple types of particles; and 3) linkers, such as linear or branched small molecule or polymer, such as poly(ethylene glycol) (PEG, e.g. multi-arm branched PEG-amines) and poly(ethylenimine) (PEI, various ratios of primary:secondary:tertiary amine groups), dendrons and dendrimers (e.g. hyperbranched bis-MPA polyester-16-hydroxyl) and chitosan, or any combination thereof. Each of the materials may incorporate the particle and the receptor components. However, incorporating the linker component is optional. Also, the labeling particles can be formulations containing various types of particles, receptors and optional linkers.

The disclosed particles in the labeling and aggregating particles can be functionalized with capturing groups ("receptors"), the structures of which can be, or derived from, cellular receptors, antibodies, or synthetically derived from available data describing interaction of target biologicals with soluble molecules. The receptors can be directly attached to the particle (FIG. 2, Mode A) or through a linker (FIG. 2, Mode B). In order to protect the integrity of the molecular structure of the particle, particularly when reuse of the labeling and aggregating particle is a requirement, one method of inter-connecting the receptors, particles and, optionally linkers, is via covalent bonding. For certain applications where added structural stability is not needed, for example in case of single use materials, physical bonding can substitute covalent bonding. The receptors play a direct role by capturing the biologicals through physical bonding. One role of the linkers is to position the receptors at an active distance from the core of the particle. By distancing the receptors from the core of the particle, the receptors can easily access the target biologicals. Another role for the linkers, particularly when they are branched, is to increase the density of the receptors on the surface of the particle (FIG. 2, Mode C). Increase in the density of receptors correlates with an increase in the capacity of capturing higher concentrations of biologicals. In some embodiments, the receptor attached to the labeling particle and the receptor attached to the aggregating particle arc the same receptor (e.g., lactose molecules may be attached to the labeling particle and to the aggregating particle). In some embodiments, the receptor attached to the labeling particle and the receptor attached to the aggregating particle are different receptors (e.g., lactose molecules may be attached to the labeling particle and heparin molecules may be attached to the aggregating particle).

Exemplary receptors in the labeling and aggregating particles can include: 1) heparin, a negatively charged polymer that mimics innate glycosaminoglycanes found in the membranes of host cells. It is commercially available as heparin sodium which is extracted from porcine intestinal mucosa and is approved as blood anti-coagulant. Also, non-animal-derived synthetic heparin-mimicking sulfonic acid polymers can act in a similar fashion to natural heparin; 2) chitosan, an ecologically friendly bio-pesticide that can ligate to a variety of micro-organisms and proteins. It is also used as a hemostatic agent and in transdermal drug delivery; and 3) lactose, a by-product of the dairy industry. It is widely available and produced annually in millions of tons. Lactose can also be synthesized by condensation/dehydration of the two sugars galactose and glucose, including all their isomers.

Exemplary particles in the labeling and aggregating particles can include metallic or magnetic particles, such as alkali, alkaline, transition, post-transition, lanthanide and actinide metal elements or compounds. Some examples of metallic or magnetic elements or compounds include, but are not limited to, lithium, sodium, potassium, rubidium, cesium, francium, beryllium, magnesium, calcium, strontium, barium, radium, aluminum, gallium, indium, tin, thallium, lead, bismuth, scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium, cerium, praseodymium, neodymium, promethium, samarium, europium, gadolinium, terbium, dysprosium, holmium, erbium, thulium, ytterbium, lutetium, thorium, protactinium, uranium, neptunium, plutonium, americium, curium, berkelium, californium, einsteinium, fermium, mendelevium, nobelium, and lawrencium, their derivatives, salts, and oxides, or any combination thereof, including combinations to form magnetic compounds. Tn one embodiment, gold nanoparticles can be the particles. In this embodiment, the smaller the size the nanoparticles is, the more red the reflected color will be. Also in this embodiment, the larger the size of the nanoparticles, the reflected color will be more blue/purple.

Other exemplary particles in the labeling and aggregating particles can include, but are not limited to, glass, silica, sand, wood, fiber, natural and synthetic polymers, rubber, copper, gold, silver, platinum, zinc, stone, stainless steel, nickel, titanium, tantalum, aluminum, Nitinol, Inconel, iridium, tungsten, silicon, magnesium, tin, alloys, and coatings containing any of the foregoing, galvanized steel, hot dipped galvanized steel, electrogalvanized steel, annealed hot dipped galvanized steel, or any combination thereof.

Glass materials suitable for use include, but are not limited to, soda lime glass, strontium glass, borosilicate glass, barium glass, glass-ceramics containing lanthanum, as well as any combination thereof.

Sand materials suitable for use include, but are not limited to, sand comprised of silica (e.g., quartz, fused quartz, crystalline silica, fumed silica, silica gel, and silica aerogel), calcium carbonate (e.g., aragonite), or any mixtures thereof. The sand can comprise other components, such as minerals (e.g., magnetite, chlorite, glauconite, gypsum, olivine, garnet), metal (e.g., iron), shells, coral, limestone, rock, or any combination thereof.

Wood materials suitable for use include, but are not limited to, hard wood and soft wood, and materials engineered from wood, wood chips, or fiber (e.g., plywood, oriented strand board, laminated veneer lumber, composites, strand lumber, chipboard, hardboard, medium density fiberboard). Types of wood include, but are not limited to, alder, birch, elm, maple, willow, walnut, cherry, oak, hickory, poplar, pine, fir, or any combination thereof.

Fiber materials suitable for use include, but are not limited to, natural fibers (e.g., derived from an animal, vegetable, or mineral) and synthetic fibers (e.g., derived from cellulose, mineral, or polymer). Suitable natural fibers include, but are not limited to, cotton, hemp, jute, flax, ramie, sisal, bagasse, wood fiber, silkworm silk, spider silk, sinew, catgut, wool, sea silk, wool, mohair, angora, and asbestos. Suitable synthetic fibers include, but are not limited to, rayon, modal, and Lyocell, metal fiber (e.g., copper, gold, silver, nickel, aluminum, iron), carbon fiber, silicon carbide fiber, bamboo fiber, seacell, nylon, polyester, polyvinyl chloride fiber (e.g., vinyon), polyolefin fiber (e.g., polyethylene, polypropylene), acrylic polyester fiber, aramid (e.g., TWARON™, KEVLAR™, or NOMEX™), spandex, or any combination thereof.

Natural polymer materials suitable for use include, but are not limited to, a polysaccharide (e.g., cotton, cellulose), shellac, amber, wool, silk, natural rubber, biopolymer (e.g., a protein, an extracellular matrix component, collagen), or any combination thereof.

Synthetic polymer materials suitable for use include, but are not limited to, polyvinylpyrrolidone, acrylics, acrylonitrile-butadiene-styrene, polyacrylonitrile, acetals, polyphenylene oxides, polyimides, polystyrene, polypropylene, polyethylene, poly(glycidyl methacrylate), polytetrafluoroethylene, polyvinylidene fluoride, polyvinyl chloride, polyethylenimine, polyesters, polyethers, polyamide, polyorthoester, polyanhydride, polysulfone, polyether sulfone, polycaprolactone, polyhydroxy-butyrate valerate, polylactones, polyurethanes, polycarbonates, polyethylene terephthalate, as well as copolymers, or any combination thereof.

Rubber materials suitable for use include, but are not limited to, silicones, fluorosilicones, nitrile rubbers, silicone rubbers, polyisoprenes, sulfur-cured rubbers, butadiene-acrylonitrile rubbers, isoprene-acrylonitrile rubbers, and the like, or any combination thereof.

Ceramic materials suitable for use include, but are not limited to, boron nitrides, silicon nitrides, aluminas, silicas, and the like, or any combination thereof.

Stone materials suitable for use include, for example, granite, quartz, quartzite, limestone, dolostone, sandstone, marble, soapstone, serpentine, or any combination thereof.

Exemplary linkers in the labeling and aggregating particles can include, but are not limited to: 1) chitosan, see its description as a receptor; 2) linear or branched Poly(ethylene glycol) and their derivatives, produced from ethylene oxides and have many different chemical, biological, commercial and industrial uses; 3) linear or branched poly (ethylenimine) (PEI, various ratios of primary:secondary: tertiary amine groups); and 4) dendrons and dendrimers, relatively new molecules. They are repetitively branched molecules using a small number of starting reagents. They are commonly used in drug delivery and in sensors.

In some embodiments, the particle at the core of the "labeling particles" can be gold nanoparticles.

In some embodiments, receptors for simultaneous detection of multiple known and unknown microorganism can include heparin and its derivatives.

In some embodiments, the receptors can be directly attached to the particle (FIG. 3) or through linkers via chemical coupling (FIG. 4). One type of coupling reagent is 1,1'-carbonyldiimidazole (CDI). However, others may be used such as N,N'-Dicyclohexylcarbodiimide (DCC) or N-(3-Dimethylaminopropyl)-N'-ethylcarbodiimide hydrochloride (EDC or EDCI).

Figure 5:
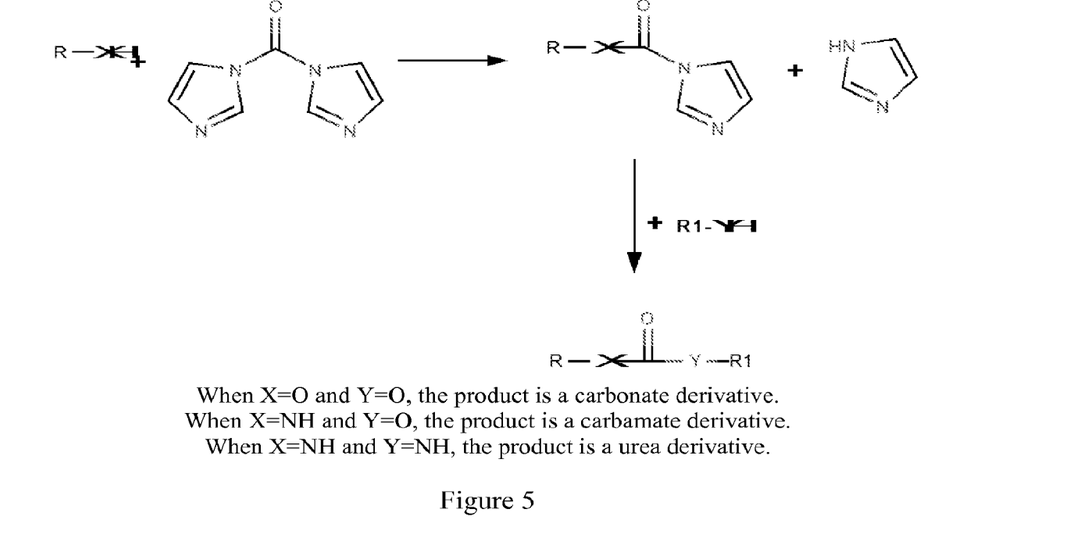
FIG. 5 illustrates a general route for covalent coupling when using 1,1'-carbonyldiimidazole.
Figure 6:
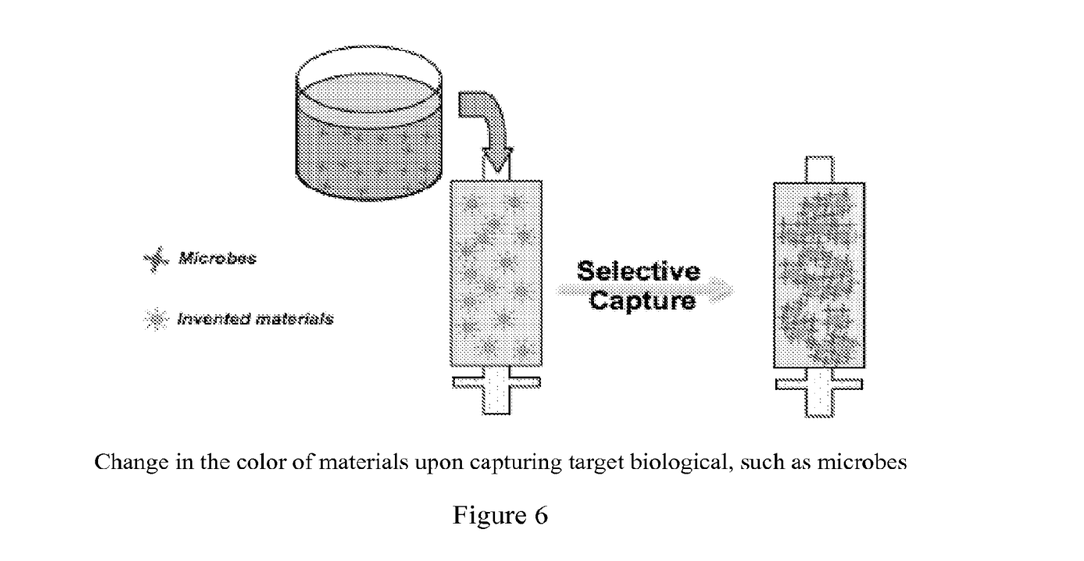
FIG. 6 illustrates a schematic representation of an application.

An exemplary coupling reagent is CDI. Basic protonated end groups, such as surface-hydrolized gold, readily react with CDI to form an ester or amide link. The resulting imidazole-substituted derivatives are reacted with hydroxyl-terminated receptors yielding either carbonates [R—O—C (O)—O-receptor] or carbamates [R—N(H)—C(O)—O-receptor]. The resulting imidazole-substituted derivatives can also be reacted with amine-terminated receptors yielding urea derivatives [R—N(H)—C(O)—N(H)-receptor] (FIG. 5). Due to the formation of a covalent bond between the receptor and the particle (direct bonding or through a linker), the structure of the bound receptor is different compared to the structure of the commercially available free receptor. For example, as depicted in FIG. 6, the receptor looses a hydrogen atom upon reaction with the immidazole-substituted derivatives to form a receptor-carbonate, receptor-carbamate or receptor-urea derivative.

If an appropriate functional group is not present on the surface of the particle, typically a suitable functional group can be made available on the surface by a chemical transformation. In general, a chemical transformation can be hydrolysis, oxidation (e.g., using Collins reagent, Dess-Martin periodinane, Jones reagent, and potassium permanganate), reduction (e.g., using sodium borohydride or lithium aluminum hydride), alkylation, deprotonation, electrophilic addition (e.g., halogenation, hydrohalogenation, hydration), hydrogenation, esterification, elimination reaction (e.g., dehydration), nucleophilic substitution, radical substitution, or a rearrangement reaction. If needed, more than one chemical transformation, successively or simultaneously, can be used to provide a suitable functional group or a heterogeneous group of functional groups of various identities. Alternatively, a monomer with a desired functional group can be grafted to the material.

In some embodiments, the chemical transformation is hydrolysis. Generally, the hydrolysis is performed with water in the presence of a strong inorganic, organic, or organo-metallic acid (e.g., strong inorganic acid, such as hydrochloric acid, sulfuric acid, phosphoric acid, nitric acid, hydroiodic acid, hydrobromic acid, chloric acid, and perchloric acid) or strong inorganic, organic, or organo-metallic base (e.g., Group I and Group II hydroxides, such as lithium hydroxide, sodium hydroxide, potassium hydroxide, rubidium hydroxide, cesium hydroxide, magnesium hydroxide, calcium hydroxide, and barium hydroxide; ammonium hydroxide; and sodium carbonate). For example, a material comprising an acyl halide can undergo hydrolysis to form a carboxylic acid.

In some embodiments, the chemical transformation is a substitution reaction where one functional group is replaced with another. For example, a material comprising a haloalkyl group can react with a strong base to form a hydroxy group.

In some embodiments, the chemical transformation is alkylation, hydrogenation, or reduction. For example, a material comprising a hydroxy or haloalkyl (e.g., iodoalkyl or bromoalkyl) moiety can be reacted with ammonia to form an amino group. A material comprising a haloalkyl moiety also can be converted to a mercapto group by S-alkylation using thiourea. A material comprising a nitrile can be hydrogenated to form an amino group. A material comprising an amido group can be reduced (e.g., in the presence of lithium aluminum hydride) to form an amino group. A material comprising a formyl or keto group can be reduced to form an amino or hydroxy group. Multiple homogeneous or heterogeneous transformations can be applied simultaneously or successively.

The labeling and aggregating particles can be formed by any suitable method using suitable temperatures (e.g., room temperature, reflux), reaction times, solvents, catalysts, and concentrations. In some embodiments, an excess amount of linkers and receptors will be used to ensure an effective amount of receptors in the labeling and aggregating particles.

In some embodiments, attachments amongst receptors, linkers, and particles can be secured physically. This is achieved by mixing receptors or linkers, or combinations thereof, dissolved in solvents with the particles, then allowing the solvents to evaporate in air or under vacuum.

In some embodiments, the particles can be mixed directly with the fluid to be tested, including fluid rinsate of solids and surfaces. The particles generally include the labeling particles. The inclusion of the aggregating particles is optional. When both types of particles are applied, the mixing of particles with the fluid to be tested can be simultaneous, where both types of particles are mixed with the fluid at the same time. It can also be successive, where one type of particle is first mixed with the fluid, followed by the other type.

Figure 9:
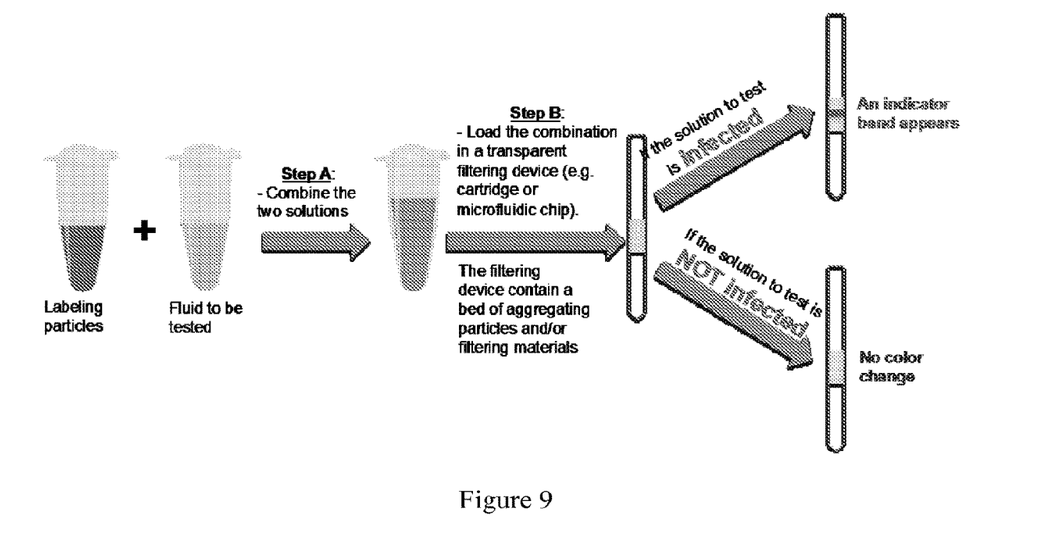
FIG. 9 illustrates examples of applications of the disclosure; such examples are classified as qualitative biological detection methods.

An exemplary application method is a qualitative test to indicate the presence or absence of target biologicals in the tested sample. The fluid to be tested is directly mixed with the labeling particles. After mixing and optional incubation, the mixture is allowed to flow through a bed of aggregating particles and/or a bed of filtering materials. The presence of target biologicals is indicated by the detection of aggregates in the bed of aggregation particles and/or the bed of filtering materials (FIG. 9). The detection of the aggregates can be achieved by the naked eye and/or by more advanced techniques, such as electronique techniques.

Figure 10:
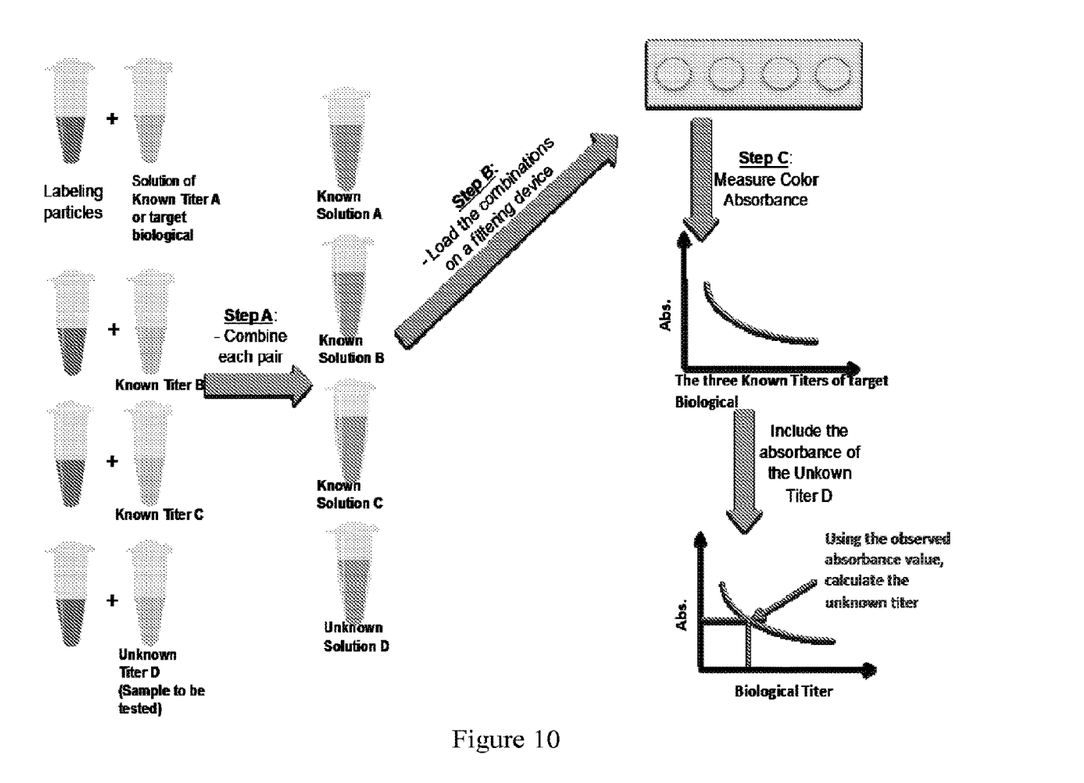
FIG. 10 illustrates examples of applications of the disclosure; such examples are classified as quantitative biological detection methods.
Figure 11:
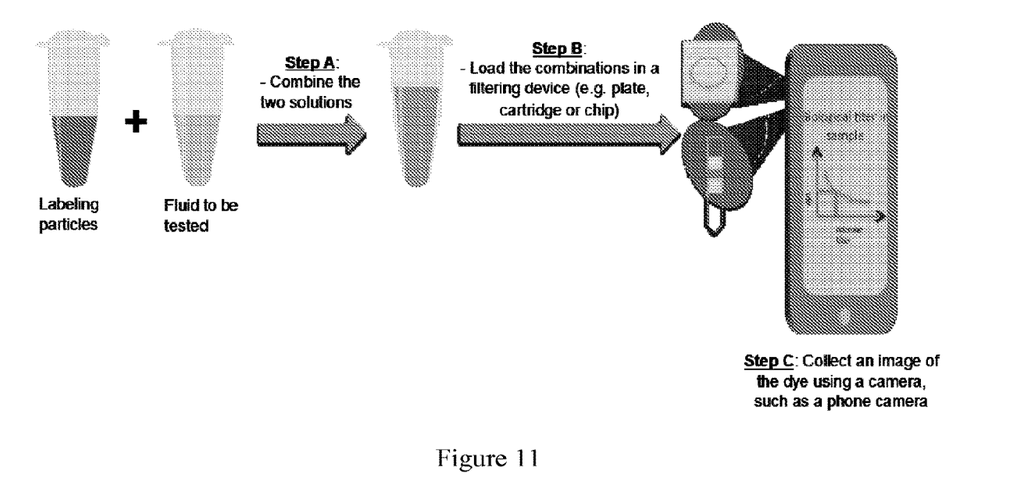
FIG. 11 illustrates examples of applications of the disclosure; such examples are classified as combination of known aggregate detection process with the invented process.

Another exemplary application method is a quantitative test to indicate the titer of target biologicals in the tested sample. The titer can be zero or larger than zero. In addition to the fluid to be tested, samples containing known titers of target biologicals are processed in this exemplary application. The fluid to be tested, containing unknown titer of target biological, and the fluids containing known titers are directly and separately mixed with the labeling particles. After mixing and optional incubation, the mixtures are allowed to flow through a bed of aggregating particles and/or a bed of filtering materials. The aggregation level of the samples containing known titers can be correlated with the known titers of the target biologicals. The presence of target biologicals in the fluid to be tested is indicated by the detection of aggregates in the bed of aggregation particles and/or the bed of filtering materials. Furthermore, the titer of the target biological is derived by comparing the aggregation level resulting from the fluid to be tested, to the aggregation levels of the samples of known titers (FIG. 10). The aggregation level of the samples can be quantified by the naked eye and/or by more advanced techniques, such as electronique techniques such as optical density measurement, color intensity quantification applications, softwares, and associated devices such as camera and camera phones (FIG. 11). A suitable method for detecting and/or quantifying the aggregation level is to correlate the value of this level to the color intensity of the aggregate.

In some embodiments, the materials can be used for point-of-use biological detection (FIG. 6). Biologicals in fluids, including air and other gases, can be detected and quantified. Examples of fluids can include, but are not limited to, water, body fluids, saliva, vomit, urine, tear, sweat, bile, breast milk, cerebrospinal fluid, feces, diarrhea, body ejaculate, body secretion, pus, mucus, lymph, gastric acid and juice, earwax, blister, humour, intracellular and extracellular fluids, blood and blood products, drinking water, waste water, industrial water, house water, plant fluids, and air.

In some embodiments, the materials can be used for point-of-use biological detection in air and other gases. Biologicals in air and other gases can be detected and quantified. One example of a method of biological detection in air is to rinse a surface that is in direct contact with the air or gas to be examined, with a fluid. After that, applying the methods described herein to examine the biologicals in the resulting fluid rinsate. In one example, the surface can be the air filter of an air-conditioning (cooling or heating) devices and systems in such environments as hospitals, malls, hotels, airplanes, boats, trains, airports, seaports, boarders, markets. In another examples, the surface can be the air filter of a breathing mask.

In some embodiments, the materials can be used for point-of-use biological detection on solids and surfaces. Biologicals on solid surfaces can be detected and quantified. One example of a method of biological detection on solid surface is to rinse the surface to be examined with a fluid. After that, applying the methods described herein to examine the biologicals in the resulting fluid rinsate. Examples of coated and un-coated solid surfaces can include, or derived from any suitable form of, such as, for example, a powder, dust, an aggregate, an amorphous solid, a sheet, a fiber, a tube, a fabric, or the like. In some embodiments, the solid surface can comprise, without being limited to, metal, glass, fiberglass, silica, sand, wood, fiber, natural polymer, synthetic polymer, plastic, rubber, ceramic, porcelain, stone, marble, cement, human or animal body, plants, food, fruit, vegetable, or meat, or any combination thereof. In other embodiments, the solid surface can comprise, without being limited to, sheet, textile, laboratory coats, coats, gloves, curtains, door handles, tables, phones, railings, keyboards, computers, screens, bottoms, elevator bottoms, etc., or any combination thereof.

The present disclosure is also directed to compositions comprising one or more of the labeling particles described herein and/or any one of more of the aggregating particles described herein, as well as kits comprising any one or more of the compositions disclosed herein, and/or reagents used for making and/or using them. In some embodiments, the compositions comprise one or more of the labeling particles described herein. In some embodiments, the compositions comprise any one of more of the aggregating particles described herein. In some embodiments, the compositions comprise any one or more of the labeling particles described herein and any one of more of the aggregating particles described herein.

The receptors may also reversibly interact with the target biologicals, such as micro-organisms or virus. The biologicals can be desorbed from the receptors, such as through elution. Eluents such as higher-then-physiological sodium chloride solutions and lactose-containing solutions are capable of desorbing the biological from the aggregating and labeling particles.

U.S. Provisional Application Ser. No. 61/784,820 filed Mar. 14, 2013 is incorporated herein by reference in its entirety.

EXAMPLES

Figure 1:
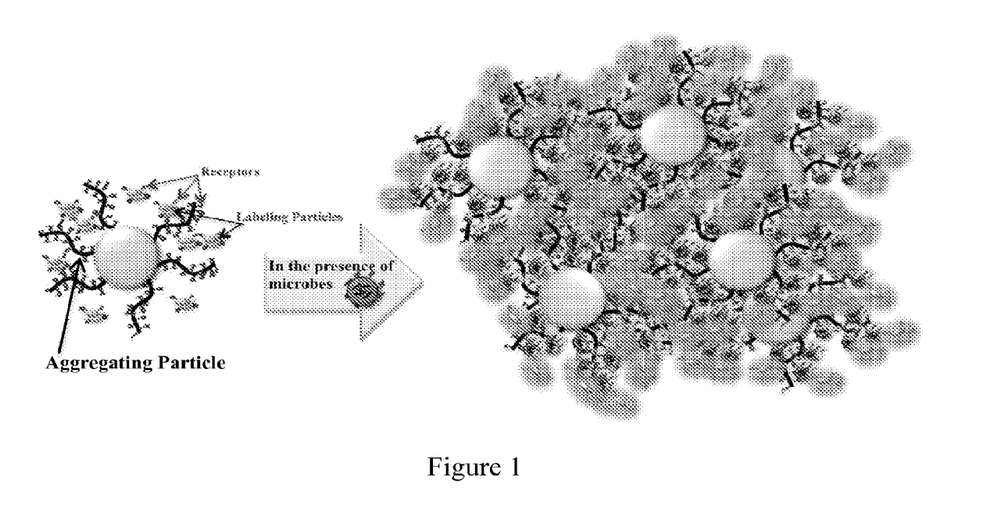
FIG. 1 illustrates the detection of biologicals, for example microbes, by forming light-scattering aggregates.
Figure 2:
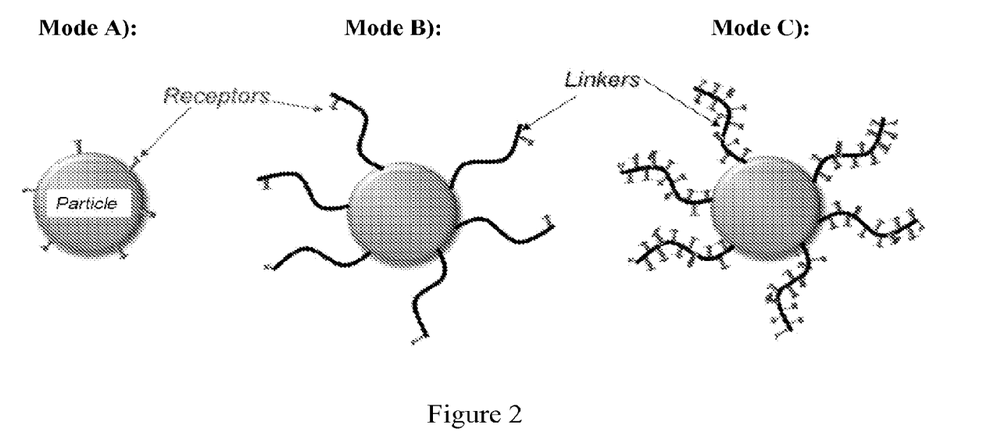
FIG. 2 illustrates three different embodiments: particles are functionalized with receptors either directly or indirectly through linkers.
Figure 3A:
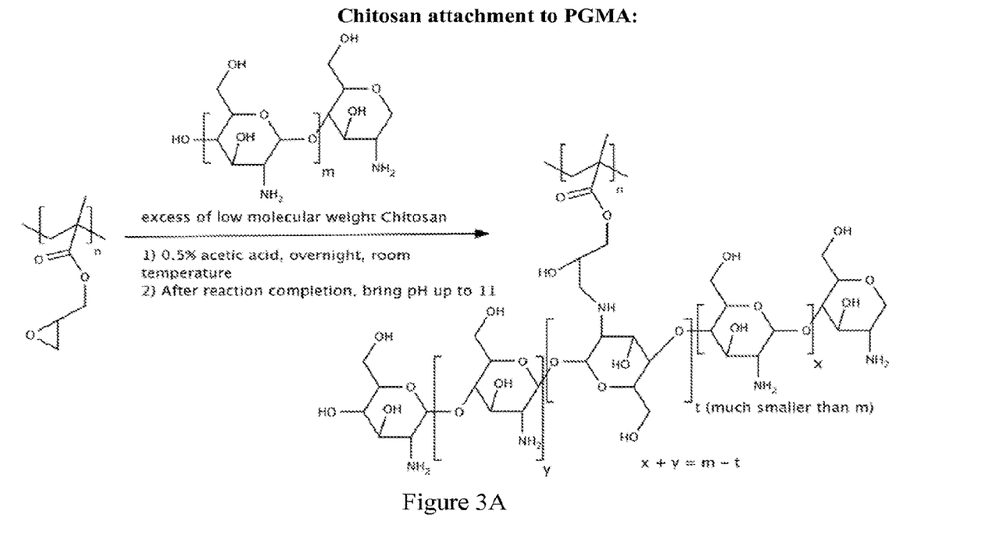
FIGS. 3A-D illustrate examples of direct attachment of receptors to particles.

Example 1: Synthesis of Chitosan-PGMA (FIG. 3A)

The synthesis followed these steps: Four hundred ml of 0.5% acetic acid in de-ionized (DI) water were prepared by adding 2 g of the acid to 400 mL of water. To this acid solution, 2 g of low molecular weight chitosan were added and the solution was allowed to stir at room temperature for 5 minutes until it became monophasic. Then, 200 mg of PGMA was added and the final suspension was allowed to stir at room temperature for two hours. The final off-white suspension was then filtered through a medium frit and the solid was washed with 100 ml of DI water. The isolated wet solid was re-suspended in 10 ml DI water. Its pH was ca. 4. One drop of a sodium carbonate solution (5 wt % sodium carbonate solution was prepared by dissolving 500 mg of $Na_2CO_3$ in 9.5 g DI water) was added to increase the pH to ca. 9. The product was isolated, rinsed with 50 ml DI water, and its wetness was preserved.

Figure 3B:
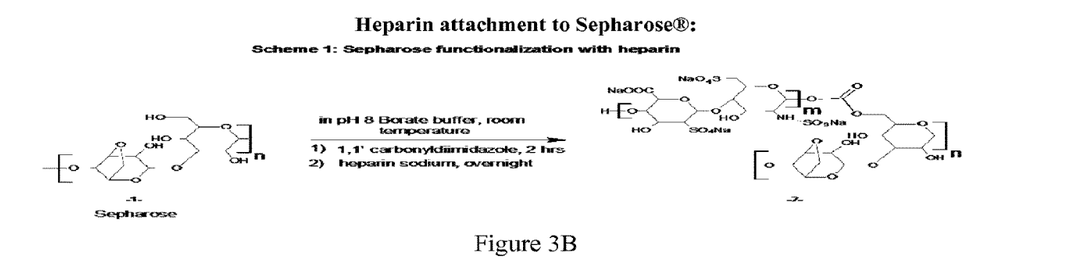

Example 2: Synthesis of Heparin-Sepharose® (FIG. 3B)

The synthesis followed these steps: 0.25 g of Sepharose® (5 wt % in water) was loaded into a 20 ml glass vial along with a stirring bar. Ten ml of pH 8.5 20 mM borate buffer was added to the solid, followed by 5 mg 1,1'-CDI. The mixture was allowed to stir for two hours and a half before the addition of 12.5 mg heparin sodium. The final mixture was allowed to stir for three days at room temperature. The product was isolated, rinsed with 25 ml DT water, and its wetness was preserved.

Figure 3C:
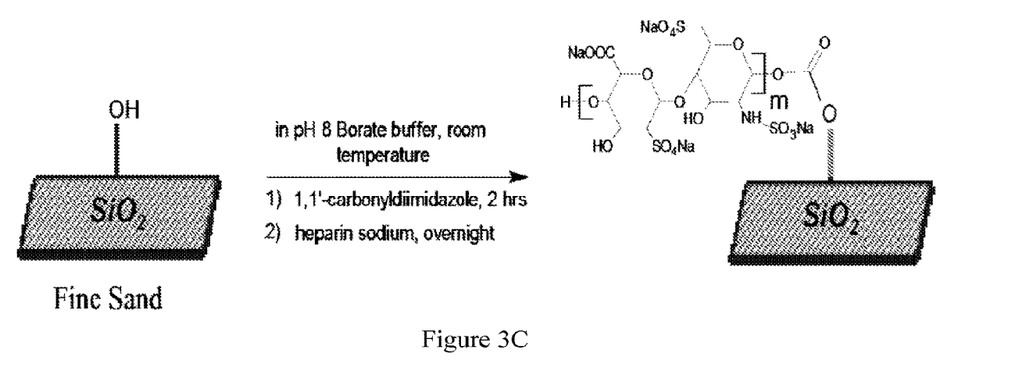

Example 3: Synthesis of Heparin-Sand (FIG. 3C)

The synthesis followed these steps: 1 g of sand was loaded into a 20 ml glass vial along with a stirring bar. Ten ml of pH 8.5 20 mM borate buffer was added to the solid, followed by 2.5 mg 1,1'-CDI. The mixture was allowed to stir for two hours and a half before the addition of 6.25 mg heparin sodium. The final mixture was allowed to stir for three days at room temperature. The product was isolated, rinsed with 50 ml DI water, and its wetness was preserved.

Figure 3D:
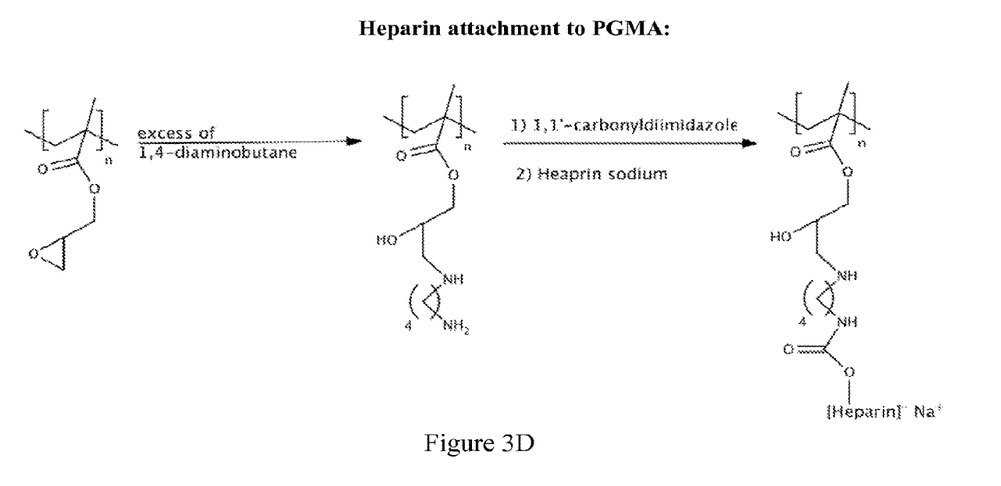

Example 4: Synthesis of Heparin-PGMA (FIG. 3D)

The synthesis followed these steps: First was the preparation of PGMA-$NH_2$: Fifty ml dry tetrahydrofuran was added to a round bottom flask, followed by 1.24 g of 1,4-diaminobutane. While stirring the solution, 200 mg PGMA were added. The solution was then allowed to stir at room temperature for 10 minutes before evacuation. To the resulting product, 50 ml DI water was added leading to the precipitation of a solid. This solid was then filtered on a medium frit and rinsed with 300 ml DT water. The following step included the preparation of heparin-PGMA: 0.05 g of PGMA-$NH_2$ was loaded into a 20 ml glass vial along with a stirring bar. Ten ml of pH 8.5 20 mM borate buffer was added to the solid, followed by 10 mg 1,1'-CDI. The mixture was allowed to stir for two hours and a half before the addition of 25 mg heparin sodium. The final mixture was allowed to stir for three days at room temperature. The final product was isolated and its wetness was preserved.

Figure 4A:
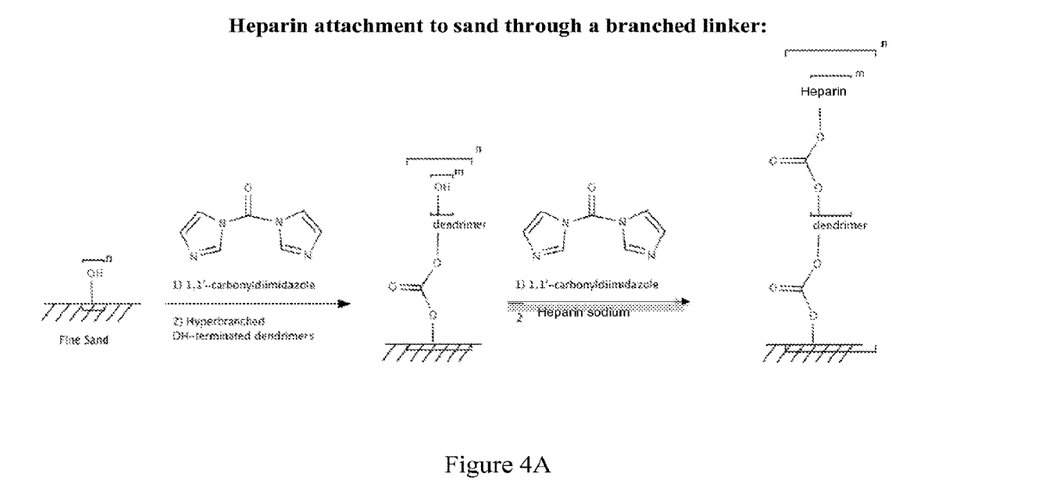
FIGS. 4A-D illustrate examples of attachment of receptors to particles via linkers.

Example 5: Synthesis of Heparin-[Branching]-Sand (FIG. 4A)

The synthesis followed these steps: One gram of fine sand was mixed with 10 ml pH 8.5 20 mM Borate buffer and allowed to stir for a few minutes at room temperature. Eight mg of 1,1'-carbonyldiimidazole was then added to the suspension and allowed to stir for 2 hours and a half before adding 0.125 g of hyperbranched bis-MPA polyester-16-hydroxyl. After an additional two hours and a half, 5 mg of 1,1'-carbonyldiimidazole was added to the suspension and allowed to stir for 2 hours before adding 12.5 mg of heparin sodium. The final mixture was allowed to stir for three days at room temperature. The final product was isolated and its wetness was preserved.

Figure 4B:
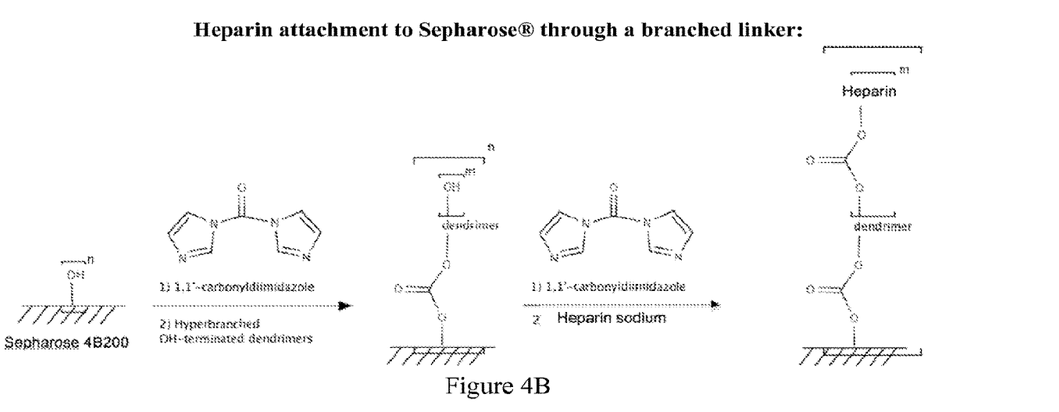

Example 6: Synthesis of Heparin-[Branching]-Sepharose® (FIG. 4B)

The synthesis followed these steps: Two hundred and fifty mg of Sepharose® (5 wt % in water) was mixed with 10 ml pH 8.5 20 mM Borate buffer and allowed to stir for few minutes at room temperature. Sixteen mg of 1,1'-carbonyldiimidazole was then added to the suspension and allowed to stir for 2 hours before adding 0.25 g of hyperbranched bis-MPA polyester-16-hydroxyl. After two hours and a half, 10 mg of 1,1'-carbonyldiimidazole was added to the suspension and allowed to stir for 2 more hours before adding 25 mg of heparin sodium. The final mixture was allowed to stir for three days at room temperature. The product was isolated, rinsed with 25 ml DI water, and its wetness was preserved.

Figure 4C:
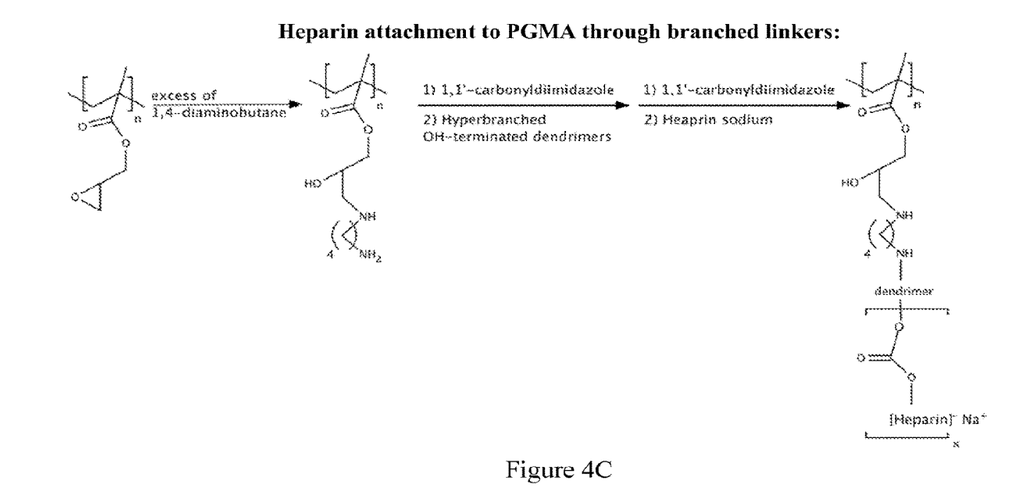

Example 7: Synthesis of Heparin-[Branching]-PGMA (FIG. 4C)

The synthesis followed these steps: Fifty mg of PGMA-NH$_2$ was mixed with 10 ml pH 8.5 20 mM Borate buffer and allowed to stir for a few minutes at room temperature. Thirty two mg of 1,1'-carbonyldiimidazole was then added to the suspension and allowed to stir for 1 hour before adding 0.5 g of hyperbranched bis-MPA polyester-16-hydroxyl. After two additional hours, 20 mg of 1,1'-carbonyldiimidazole was added to the suspension and allowed to stir for 2 more hours before adding 50 mg of heparin sodium. The final mixture was allowed to stir for three days at room temperature. The product was isolated, rinsed with 25 ml DI water, and its wetness was preserved.

Figure 4D:
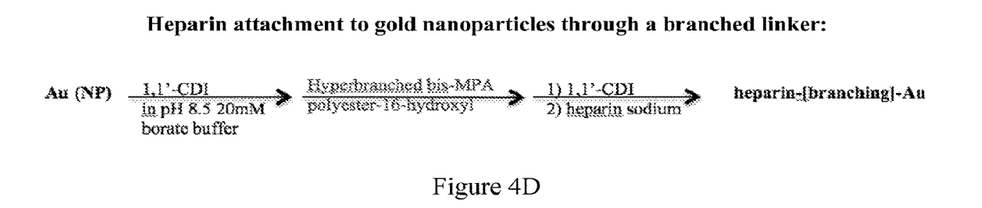

Example 8: Synthesis of Heparin-[Branching]-Gold Nanoparticles (FIG. 4D)

The synthesis followed these steps: Five ml of gold nanoparticle solution in PBS was mixed with 2 ml pH 8.5 20 mM Borate buffer and allowed to stir for 30 minutes at room temperature in a glass vial. Eight mg of 1,1'-carbonyldiimidazole (0.05 mmol, MW 162.15) was then added to the suspension and allowed to stir for 2 hours before adding 0.133 g of hyperbranched bis-MPA polyester-16-hydroxyl. After that, 20 mg of 1,1'-carbonyldiimidazole was added to the suspension and allowed to stir for 2 hours before adding 50 mg of heparin sodium. The final mixture was allowed to stir overnight at room temperature.

Example 9: Synthesis of Heparin-[Branching]-Sand

The synthesis will follow these steps: One gram of fine sand will be mixed with 10 ml pH 8.5 20 mM Borate buffer and allowed to stir for a few minutes at room temperature. Eight mg of 1,1'-carbonyldiimidazole will then be added to the suspension and allowed to stir for 2 hours and a half before adding branched poly(ethylene glycol) (1.14 mmol.eq. OH). After an additional two hours and a half, 5 mg of 1,1'-carbonyldiimidazole will be added to the suspension and allowed to stir for 2 hours before adding 12.5 mg of heparin sodium. The final mixture will be allowed to stir for three days at room temperature. The final product will be isolated and its wetness will be preserved.

Example 10: Synthesis of Heparin-[Branching]-Sepharose®

The synthesis will follow these steps: Two hundred and fifty mg of Sepharose® (5 wt % in water) will be mixed with 10 ml pH 8.5 20 mM Borate buffer and allowed to stir for a few minutes at room temperature. Sixteen mg of 1,1'-carbonyldiimidazole will then be added to the suspension and allowed to stir for 2 hours before adding branched poly(ethylene glycol) (2.28 mmol.eq. OH). After two hours and a half, 10 mg of 1,1'-carbonyldiimidazole will be added to the suspension and allowed to stir for 2 more hours before adding 25 mg of heparin sodium. The final mixture will be allowed to stir for three days at room temperature. The product will be isolated, rinsed with 25 ml DI water, and its wetness will be preserved.

Example 11: Synthesis of Heparin-[Branching]-PGMA

The synthesis will follow these steps: Fifty mg of PGMA-NH$_2$ will be mixed with 10 ml pH 8.5 20 mM Borate buffer and allowed to stir for a few minutes at room temperature. Thirty two mg of 1,1'-carbonyldiimidazole will then be added to the suspension and allowed to stir for 1 hour before adding branched poly(ethylene glycol) (4.56 mmol.eq. OH). After two additional hours, 20 mg of 1,1'-carbonyldiimidazole will be added to the suspension and allowed to stir for 2 more hours before adding 50 mg of heparin sodium. The final mixture will be allowed to stir for three days at room temperature. The product will be isolated, rinsed with 25 ml DI water, and its wetness will be preserved.

Example 12: Synthesis of Heparin-[Branching]-Gold Nanoparticles

The synthesis will follow these steps: Five ml of gold nanoparticle solution in PBS will be mixed with 2 ml pH 8.5 20 mM Borate buffer and allowed to stir for 30 minutes at room temperature in a glass vial. Eight mg of 1,1'-carbonyldiimidazole (0.05 mmol, MW 162.15) will then be added to the suspension and allowed to stir for 2 hours before adding branched poly(ethylene glycol) (1.14 mmol.eq. OH). After that, 20 mg of 1,1'-carbonyldiimidazole will be added to the suspension and allowed to stir for a 2 hours before adding 50 mg of heparin sodium. The final mixture will be allowed to stir overnight at room temperature.

Example 13: Infected Surface Water

Figure 7:
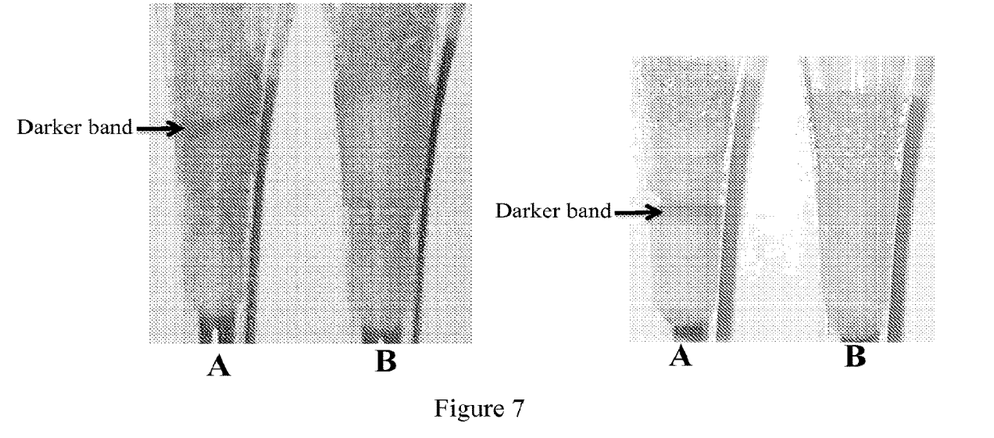
FIG. 7 illustrates aggregation of the labeling particles, functionalized gold nanoparticles, with aggregating particles, functionalized sand.

One hundred µl of surface water (non-potable but clear) from Lexington, Mass., was mixed with 50 µl of the heparin-[branching]-gold nanoparticles solution. The resulting solution was designated as solution A. 100 µl of potable clean water was mixed with 50 µl of the heparin-[branching]-gold nanoparticles solution. The resulting solution was designated as solution B. Both solutions, A and B, were mixed. Two Pasteur glass pipettes were stopped with cotton followed by heparin-[branching]-sand. These pipettes were then loaded with either solution A or B. The solutions were allowed to sit on sand for 10 minutes before slowly forcing them through the sand beds. The cotton layer in column A, where solution A was loaded, showed a dark red band, while the cotton layer in column B, where solution B was loaded, did not show a dark red band (Examples in FIG. 7).

Example 14: Infected Surface Water

Figure 8:
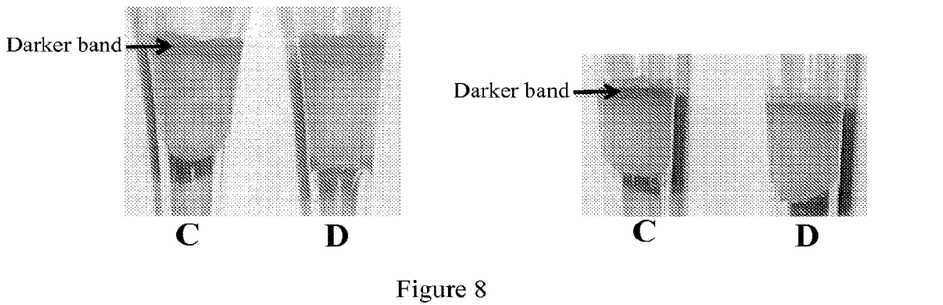
FIG. 8 illustrates aggregation of the labeling particles, functionalized gold nanoparticles, with aggregating particles, functionalized PGMA.

One hundred µl of surface water (non-potable but clear) from Lexington, Mass., was mixed with 50 µl of the heparin-[branching]-gold nanoparticles solution. The resulting solution was designated as solution C. One hundred µl of potable clean water was mixed with 50 µl of the heparin-[branching]-gold nanoparticles solution. The resulting solution was designated as solution D. Both solutions, C and D, were mixed. To each of the solutions, C and D, 5 mg of heparin-[branching]-PGMA was added and allowed to mix. Two Pasteur glass pipettes were stopped with cotton. Solution C was loaded into the first pipette and solution D was loaded into the second pipette. The solutions were allowed to slowly migrate through the pipettes. The outcome bed in the first pipette, where solution C was loaded, showed a dark red to brown band, while the outcome bed in the second pipette, where solution D was loaded, did not show this dark band (Examples in FIG. 8).

Example 15: Infected Surface Water

One hundred µl of surface water (non-potable but clear) from Lexington, Mass., was mixed with 50 µl of the heparin-

[branching]-gold nanoparticles solution. The resulting solution was designated as solution E. One hundred μl of potable clean water was mixed with 50 μl of the heparin-[branching]-gold nanoparticles solution. The resulting solution was designated as solution F. Both solutions, E and F, were mixed. To each of the solutions E and F, 5 mg of heparin-Sepharose® was added and allowed to mix at 200 rpm for 5 minutes. Two Pasteur glass pipettes were stopped with cotton. Solution E was loaded into the first pipette and solution F was loaded into the second pipette. The solutions were allowed to slowly migrate through the pipettes. Difference in coloration was observed between the two beds in the first and the second pipette.

Example 16: Aqueous Solutions of Known Bacteria Titers

Preparation of the *Escherichia coli* (*E. coli*) inoculum: Lysogeny broth (LB) (1 mL) was added to a 15 ml cell culture tube. Seven (7) μl of 40% glycerol stock of the ONE SHOT™ TOP10 *E. coli* cells (Life Technologies, Grand Island, N.Y.) was inoculated into the 1 ml LB broth. The inoculate was incubated at 37° C. for 3 hours with constant shaking (ca. 250 rpm). The inoculate was then centrifuged at 2500 rpm speed for 4 minutes. The LB broth was separated, and the *E. coli* cells were washed twice with 1 ml of sterile phosphate buffered saline (PBS) 1× (pH 7.4) each time and then re-suspended in 1 mL of the same buffer. Using optical density measurements, the final bacterium titer was estimated to be ca. $5 \times 10^7$ cells/ml. This solution was labeled Solution 84-1. Ten μl of Solution 84-1 was mixed with 990 μl of sterile PBS 1×. The resulting bacterium titer was estimated at $5 \times 10^5$ cells/ml. This solution was labeled Solution 84-2. Ten μl of Solution 84-2 was mixed with 990 μl of sterile PBS 1×. The resulting bacterium titer was estimated at $5 \times 10^3$ cells/ml. This solution was labeled Solution 84-3. Ten μl of Solution 84-3 was mixed with 990 μl of sterile PBS 1×. The resulting bacterium titer was estimated at 50 cells/ml. This solution was labeled Solution 84-4.

Example 17: Aqueous Solutions of Known Bacteria Titers

Figure 12:
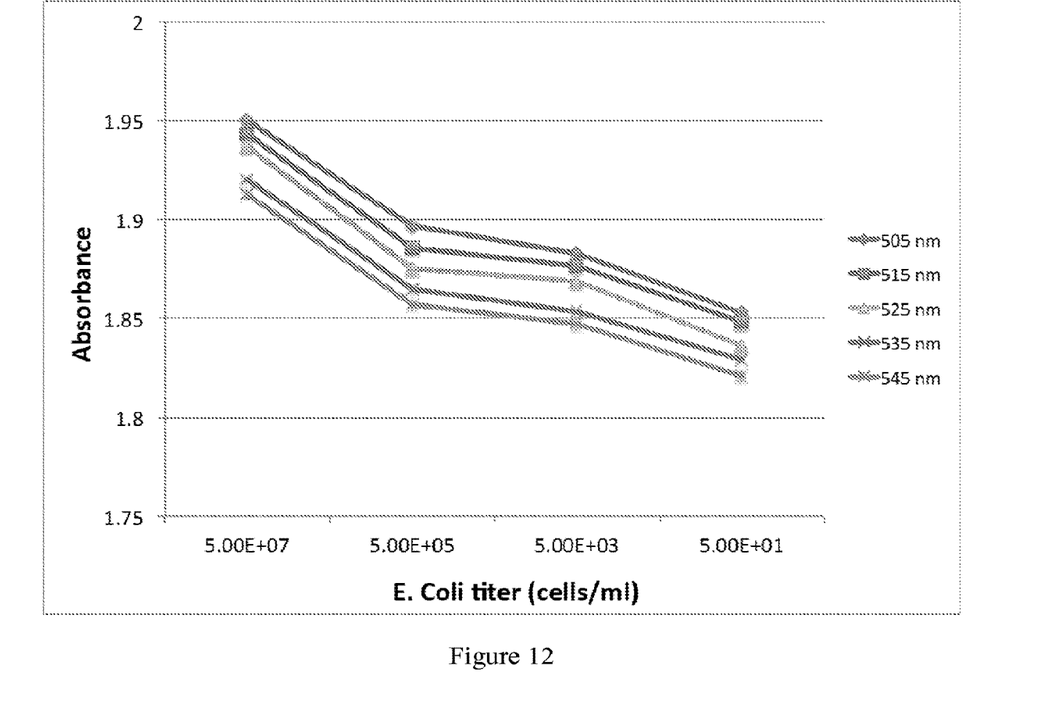
FIG. 12 illustrates examples of results showing a correlation between the Absorbance of *Escherichia coli* bacteria aggregates and the titer of *Escherichia coli* bacteria in the examined solutions.

Correlation of the *Escherichia coli* (*E. coli*) titer with the color intensity of the formed aggregates: 200 μl of each of the above Solutions 84-1, 84-2, 84-3, 84-4 were mixed with 25 μl of heparin-[branching]-gold nanoparticles solution. The resulting solutions were passed through 96-well filter plates (Millipore MAFCNOB). The Absorbance values in these wells were then read using a Tecan plate reader (FIG. 12). Absorbance reading (Abs.) at 505 nm wavelength revealed the following values: 1) for Solution 84-1, Abs. 1.9505; 2) for Solution 84-2, Abs. 1.8965; 3) for Solution 84-3, Abs. 1.8829; 4) for Solution 84-4, Abs. 1.8527. Absorbance reading (Abs.) at 515 nm wavelength revealed the following values: 1) for Solution 84-1, Abs. 1.9434; 2) for Solution 84-2, Abs. 1.8853; 3) for Solution 84-3, Abs. 1.8764; 4) for Solution 84-4, Abs. 1.8482. Absorbance reading (Abs.) at 525 nm wavelength revealed the following values: 1) for Solution 84-1, Abs. 1.9373; 2) for Solution 84-2, Abs. 1.8750; 3) for Solution 84-3, Abs. 1.8685; 4) for Solution 84-4, Abs. 1.8363. Absorbance reading (Abs.) at 535 nm wavelength revealed the following values: 1) for Solution 84-1, Abs. 1.9202; 2) for Solution 84-2, Abs. 1.8646; 3) for Solution 84-3, Abs. 1.8537; 4) for Solution 84-4, Abs. 1.8288. Absorbance reading (Abs.) at 545 nm wavelength revealed the following values: 1) for Solution 84-1, Abs. 1.9125; 2) for Solution 84-2, Abs. 1.8573; 3) for Solution 84-3, Abs. 1.8475; 4) for Solution 84-4, Abs. 1.8209.

The invention claimed is:

1. A method for detecting a biological comprising:
   mixing a sample with a plurality of particles each of which comprises a receptor adapted for binding to the biological such that said particles form one or more aggregates if said biological is present in the sample and binds to the receptor; and
   identifying presence of the biological in the sample by detecting one or more aggregates of said particles,
   wherein at least one of the particles further comprises a covalently bonded linker molecule, and wherein the receptor is covalently bonded to the particle via said linker molecule, and
   wherein the linker molecule is a dendron, a dendrimer, or a combination thereof.

2. The method of claim 1, wherein said linker molecule is a dendron.

3. The method of claim 2, wherein said dendron is a hyperbranched dendron.

4. The method of claim 1, wherein said linker molecule is a dendrimer.

5. The method of claim 4, wherein said dendrimer is a hyperbranched dendrimer.

6. The method of claim 1, wherein at least one of said particles is any of a light absorbing particle, a reflecting particle, a scattering particle, a metallic particle, a magnetic particle, or any combinations thereof.

7. The method of claim 1, wherein said receptor is selected from the group consisting of lactose, lactose derivative, mono- or poly-saccharide, heparin, chitosan, or any combinations thereof.

8. The method of claim 1, wherein at least one of said particles is an absorbing, reflecting or scattering particle, metallic particle, magnetic particle, agarose, polysaccharide, natural sand, processed sand, textile, cellulose, cotton, wool, nylon, polyester, nanoparticle, glass, fiberglass, silica, wood, fiber, plastic, rubber, ceramic, porcelain, stone, marble, cement, biological polymer, natural polymer, synthetic polymer, or any combinations thereof of various particle sizes.

9. The method of claim 8, wherein said metallic particle is a gold particle or nanoparticle, or a silver particle or nanoparticle, or any combinations thereof.

10. The method of claim 8, wherein said synthetic polymer is poly(glycidyl methacrylate) (PGMA), PGMA-NH$_2$, or a combination thereof.

11. The method of claim 8, wherein said natural polymer is cotton.

12. The method of claim 1, further comprising separating said one or more aggregates from the sample using filtration, decantation, magnetism, or any combinations thereof.

13. The method of claim 1, wherein said biological is selected from the group consisting of cell, tissue, tissue product, blood, blood product, body fluid, product of body fluid, protein, vaccine, antigen, antitoxin, biological medicine, biological treatment, virus, microorganism, fungus, yeast, alga, bacterium, prokaryote, eukaryote, *Staphylococcus aureus, Streptococcus, Escherichia coli* (*E. coli*), *Pseudomonas aeruginosa, Mycobacterium*, adenovirus, rhinovirus, smallpox virus, influenza virus, herpes virus, human immunodeficiency virus (HIV), rabies virus, chikungunya virus, severe acute respiratory syndrome (SARS) virus, polio virus, malaria parasite, dengue fever virus, tuberculosis bacterium, meningitis microorganism, typhoid fever bacterium, yellow fever virus, ebola virus, *Shigella*,

*Listeria, Yersinia*, West Nile virus, protozoa, fungi, *Salmonella enterica, Candida albicans, Trichophyton mentagrophytes*, poliovirus, *Enterobacter aerogenes, Salmonella typhi, Klebsiella pneumoniae, Aspergillus brasiliensis*, and methicillin resistant *Staphylococcus aureus* (MRSA), or any combinations thereof.

14. The method of claim 1, wherein said sample is a fluid selected from the group consisting of water, juices, fluid extracts, body fluids, saliva, vomit, urine, tear, sweat, bile, milk, breast milk, cerebrospinal fluid, feces, diarrhea, body ejaculate, body secretion, pus, mucus, lymph, gastric acid and juice, earwax, blister, humoral fluid, intracellular and extracellular fluids, blood and blood products, drinking water, waste water, industrial water, house water, plant fluids, rinsates of solid and surface, rinsates of food, rinsates of fruits, rinsates of vegetables, air, and gas, or any combination thereof, and wherein the rinsates of solid and surface are rinsates of a solid and/or a surface selected from the group consisting of coated and un-coated powder, dust, aggregate, amorphous solid, crystalline solid, sheet, fiber, tube, fabric, metal, glass, fiberglass, silica, sand, wood, fiber, natural polymer, synthetic polymer, plastic, rubber, ceramic, porcelain, stone, marble, cement, human or animal body, plant, food, fruit, vegetable, meat, textile, coat, glove, curtain, door handle, table, phone, railing, keyboard, computer, screen, button, or any combinations thereof.

15. The method of claim 1, wherein the detection of said one or more aggregates of the particles is performed via visual inspection.

16. The method of claim 1, wherein the detection of said one or more aggregates of the particles is performed via color density measurement, optical density measurement, or a combination thereof.

17. The method of claim 1, further comprising quantifying aggregation level of said particles in the sample.

18. The method of claim 17, wherein said step of quantifying the aggregation level of said particles is performed by any of visual inspection, optical density measurement, and color intensity quantification.

19. The method of claim 17, further comprising comparing the aggregation level of said particles in the sample with aggregation level of one or more samples of known titers to obtain concentration of the biological in the sample.

20. The method of claim 1, wherein a first plurality of said particles is bound to one receptor type and a second plurality of said particles is bound to a different receptor type.

* * * * *